US 6,699,187 B2

(12) United States Patent
Webb et al.

(10) Patent No.: US 6,699,187 B2
(45) Date of Patent: Mar. 2, 2004

(54) SYSTEM AND METHOD FOR PROVIDING REMOTE EXPERT COMMUNICATIONS AND VIDEO CAPABILITIES FOR USE DURING A MEDICAL PROCEDURE

(75) Inventors: James D. Webb, Maple Grove, MN (US); C. Gary Nelson, Plymouth, MN (US); James G. Thies, Champlin, MN (US); Ronald A. Stauffer, Princeton, MN (US)

(73) Assignee: Medtronic, Inc., Minneapolis, MN (US)

( * ) Notice: Subject to any disclaimer, the term of this patent is extended or adjusted under 35 U.S.C. 154(b) by 70 days.

(21) Appl. No.: 09/815,728

(22) Filed: Mar. 26, 2001

(65) Prior Publication Data

US 2001/0037366 A1 Nov. 1, 2001

Related U.S. Application Data

(63) Continuation-in-part of application No. 09/381,263, filed as application No. PCT/US98/06085 on Mar. 27, 1998, now Pat. No. 6,325,756.
(60) Provisional application No. 60/042,367, filed on Mar. 27, 1997, and provisional application No. 60/192,006, filed on Mar. 24, 2001.

(51) Int. Cl.⁷ .............................. A61B 5/00; A61N 1/00; G09G 5/00
(52) U.S. Cl. .................. 600/300; 607/30; 128/904; 345/754
(58) Field of Search ................................ 600/300, 301; 607/30–32, 60; 128/903, 904; 340/573.1; 378/63; 348/14.01–14.16; 709/202, 204, 205; 345/751, 753, 754, 759

(56) References Cited

U.S. PATENT DOCUMENTS 4,098,267 A    7/1978  Stein et al. ............ 128/2.06 G
4,317,956 A    3/1982  Torok et al. ................... 178/18
4,377,852 A    3/1983  Thompson ................... 364/900
5,168,269 A    12/1992 Harlan ....................... 340/709
5,193,535 A    3/1993  Bardy et al. ................. 128/419
5,235,680 A    8/1993  Bijnagte ..................... 395/161
5,241,625 A    8/1993  Epard et al. ................. 395/163
5,263,869 A    11/1993 Ziv-El ........................ 434/336
5,384,643 A    1/1995  Inga et al. ................... 358/403
5,452,299 A    9/1995  Thessin et al. ............... 370/62
5,605,531 A  * 2/1997  Lane et al. ................... 378/63
5,696,492 A  * 12/1997 Sakamaki et al. ........ 340/573.1
5,720,770 A  * 2/1998  Nappholz et al. ............. 607/30
5,961,446 A  * 10/1999 Beller et al. ................ 128/904
6,115,027 A  * 9/2000  Hao et al. ................... 709/202
6,203,495 B1 * 3/2001  Bardy ......................... 600/301
6,418,346 B1 * 7/2002  Nelson et al. ................. 607/30

FOREIGN PATENT DOCUMENTS

WO        WO 99/14882   *   3/1999

* cited by examiner

Primary Examiner—Eric F. Winakur
Assistant Examiner—David J. McCrosky

(57) ABSTRACT

A system is described for allowing medical data obtained at a local site to be transferred to a data processing system located at a remote site. This medical data may include video data and/or data obtained from one or more medical devices such as a fluoroscopy device or an electrocardiograph (ECG) signal monitoring device. The data may be viewed on one or more display windows of the remote data processing system to allow a remotely-located expert to participate in an examination or medical procedure being conducted at the local site. In one embodiment, the remote data processing system also receives screen data from an implantable medical device programmer that is located at the local site. This screen data may include data associated with the configuration of the programmer, the configuration of an implantable medical device, and other information obtained from a patient such as physiological waveforms. Routing of all data may be performed by a communication hub operating as a stand alone device. Alternatively, the data routing function may be implemented on the programmer.

31 Claims, 12 Drawing Sheets

FIG. 11

SYSTEM AND METHOD FOR PROVIDING REMOTE EXPERT COMMUNICATIONS AND VIDEO CAPABILITIES FOR USE DURING A MEDICAL PROCEDURE

RELATED APPLICATIONS

This application is a continuation-in-part of U.S. patent application Ser. No. 09/381,263 filed Sep. 17, 1999, now, U.S. Pat. No. 6,325,756, which is incorporated herein by reference in its entirety and is a 371 of PCT/US98/06085 filed Mar. 27, 1995, which claims the benefit of provisional application 60/042,367 filed Mar. 27, 1997.

This application further claims priority to provisionally-filed U.S. Patent application No. 60/192,006 filed Mar. 24, 2001, which is incorporated herein by reference in its entirety.

FIELD OF THE INVENTION

This invention relates generally to a medical communication system; and, more particular, to a system and method for enabling a remotely-located clinician to participate in, and provide advice, during a surgical medical being performed at a different location.

BACKGROUND OF THE INVENTION

Many medical procedures such as the implantation of medical devices require the cooperation and coordination of various surgical and other medical skills. While the necessary surgical skills are filled by surgeons or other physicians, the need for other technical expertise usually necessitates the presence of a field representative or other technical personnel.

While some prior art medical communications systems have been provided to facilitate the cooperation of multiple medical experts located at different locations, these solutions are not particularly well suited to the surgical or clinical environments. One example of a communication system for use in medical applications is the model 89441a Vector Signal Analyzer(™) from Hewlett Packard. This system allows a remote expert to control screen data being displayed on a workstation located at the site of the medical procedure. However, this system does not allow the remotely-located expert to view real-time physiological data and/or video data captured during the procedure. Moreover, this system does not allow screen data replicated at both local and remote sites to be interactively manipulated, as by use of a pointer, at either of the locations.

Other prior art communications systems are described in the following U.S. patents:

U.S. Pat. No. 5,241,625, issued to Epard et al. discloses a system for remotely observing and optionally controlling information, including text and graphical images that are displayed on a computer from among both homogeneous and heterogeneous computers coupled in a network or via other transport media such as magnetic disks captures window system event messages during a recording process. Such messages are then translated into procedure calls during the imaging process on the destination platform.

U.S. Pat. No. 5,384,643, issued to Inga et al. discloses a storage, retrieval, and transmission system that is configured to provide fast, efficient telecommunication access to digitized images (e.g., medical diagnostic X-ray images) to multiple requesting subscribers. Image data are downloaded, via the telephone lines, to a remote display terminal in an optimal fashion that employs a two-dimensional patterned data compression scheme. The data compression methods include a "Hex-Pac" compression in which one first generates regions comprising a plurality of two dimensional, non-overlapping, symmetrically disposed super pixels that are collectively representative of an image. Each of these regions is subsequently compared with a plurality of fictitious patterns, each of which has a dark region, a light region and a predetermined point of origin, in order to determine which of the patterns most closely correlates with the selected region.

U.S. Pat. No. 4,377,852, issued to Thompson discloses a communications control system for enabling a small computer system, such as a personal computer, to emulate a terminal and thus to communicate with a remote system. Incoming data from the remote system is entered into a circular buffer on an interrupt basis. The communications control system alternately scans the circular buffer for newly entered data and the keyboard for operator generated messages. Any control characters are decoded and appropriate actions taken. Received alphanumeric characters are stored in a display memory for video display and in a system RAM for later retrieval and study.

U.S. Pat. No. 5,263,869, issued to Ziv-El, which discloses a computerized teaching system is described, which comprises an interactive group communication system, wherein students in a first group interact with a teacher in Social Mode, and, in some case, while students in a second group proceed with work in Independent Mode.

U.S. Pat. No. 5,452,299, issued to Thessin et al. discloses a method and apparatus for communication between agents in an electronic conferencing system. In an electronic conferencing system wherein data is shared between a plurality of participants during an electronic conference, a method is disclosed for transferring large object data blocks among the participants during the electronic conference comprising the following steps: a) receiving an asynchronous request for large object data; b) placing the request in a request queue; c) receiving an asynchronous request for reprioritization of the request queue; d) determining a transport medium capability; e) partitioning the large object data into data blocks, a size of the data blocks being variable and corresponding to the capability of the transport medium; f) transferring the requested large object data to each of the participants via the transport medium; and g) removing the request from the request queue upon completion of the step of sending the requested large object data.

U.S. Pat. No. 5,168,269, issued to Harlan discloses a system which has a first computer (herein termed the SUPPORT PC) and second remotely located computer (herein termed the CUSTOMER PC). The SUPPORT PC and the CUSTOMER PC each have a display. The image displayed on the CUSTOMER PC's display is transmitted to and duplicated on the SUPPORT PC's display. The SUPPORT PC is equipped with an analog input device (such as a mouse), the efficient operation of which requires immediate visual feedback. Signals from the input device are transmitted to the remote CUSTOMER PC. The images which appear on the display of the remote CUSTOMER PC are transmitted, relatively slowly, to the display of the SUPPORT PC. In order to provide immediate visual feedback to the operator of the input device at the SUPPORT PC, a Dynamic Temporary Dual Cursor is shown on the screen of the SUPPORT PC along with the regular cursor which is transmitted from the CUSTOMER PC. The Dynamic Temporary Dual Cursor is moved in quick synchronization with movement of the input device in direct response to the input device.

U.S. Pat. No. 4,317,956 issued to Torok et al. discloses a telautograph system that allows a user at one location to write on a special surface, such as a chalkboard, and have the image appear at remote screens. Presently, a user wishing to call attention to an entry already written on the board must make a new line or must circle the item to which the remote viewer's attention is to be drawn. This procedure unduly clutters the image and a system has been devised which provides for a cursor (a graphical hand) to appear on the remote screen when the user touches the input surface at a point. The cursor also appears when the user is writing on the surface so as to call attention to the newly formed images.

U.S. Pat. No. 4,098,267, issued to Stein et al. discloses a system for displaying several lines of electrocardiographic (ECG) signals on a cathode ray tube screen for observation, analysis and selection of those portions of the signals which indicate abnormalities of heart rhythm and cardiac events of interest to the diagnostician or trained observer. The ECG signals may be recorded at real time but are inputted to the system at much greater than real time. The system provides the display of the signal portions which were recorded consecutively, each on a separate vertically displayed line. Together with the ECG signals, other alphanumeric data, such as the time of day when the signals were recorded, patient name, heart rate, cardiac condition, and other pertinent information, may also be displayed simultaneously with the lines of ECG signals by the use of the memory and storage means to receive and hold such data. As consecutive sets of lines of the ECG signals are presented for display, sections of each line containing abnormalities and cardiac events of interest may be identified by an observer and transferred through the memory to the storage unit.

U.S. Pat. No. 5,235,680, issued to Bijnagte, discloses a system and method for storing, retrieving displaying, printing and otherwise manipulating color images stored in a central "host" computer from a realtor's remote data terminal includes a host computer which stores and maintains a database containing listings of real estate properties on the market. The host computer also optionally can store image information relating to specific properties. Images can be loaded from remote terminals over telephone lines to the host system on an interactive basis. Images can then be retrieved from the host system, also on an interactive basis, for display, printing, or storage on a storage medium associated with the remote display terminals. Images may also be deleted on an interactive basis from a remote terminal.

What is needed, therefore, is an improved communications system for displaying in real-time, or near real-time, physiological signal data at multiple locations. This signal data includes the position of a pointer that may be manipulated at multiple locations so that communication is facilitated between the various experts discussing and viewing the data, and further includes video data obtained from the patient site.

SUMMARY OF THE INVENTION

The current invention provides a system for allowing medical data obtained at a first (local) site to be transferred to a second, remote site. This medical data may include video data and/or data obtained from one or more medical devices such as a fluoroscopy device or an electrocardiograph (ECG) signal monitor.

The inventive system includes a communications network located at a first site such as a clinic or hospital where a medical procedure or a patient examination is being conducted. This communications network may be coupled to a video device such as a camera adapted to obtain video-formatted data of the procedure. The video device may be adapted to also provide an audio signal. Video data obtained at the first site may be transferred over the communications network to the remote site. At the remote site, a data processing system such as a personal computer or a programmer for programming an implantable medical device (IMD) is executing software that allows the video data to be received and viewed on a display screen. In one embodiment of the invention, the data processing system displays the video data in substantially real-time. In this manner, a remotely-located expert is allowed to view a procedure occurring at the first location.

As discussed above, many types of data may be transferred to the remote data processing system. In one embodiment, an x-ray fluoroscopy device is used to obtain an image of fluoro-visible media that is located within a patient's body. This image may be transferred to the remote system for viewing on the display screen of the data processing system. In another embodiment, an ECG signal may be obtained from a device intercoupled to the patient via electrodes located on the patient's body. This ECG signal may be transferred via the communications network to be viewed on the remote system.

Yet another type of device that may be coupled to the communications network is a programmer of the type used to program IMDs. Programmers may be used to both display patient data retrieved from an IMD including an electrodcardiogram (EGM) of a patient's heart, and to initialize and modify the configuration of the IMD. In one embodiment of the invention, screen data being displayed by a programmer located at the local site is transferred for display at the remote site. Additionally, cursor movements as controlled by a clinician at the local site are also displayed to an expert at the remote site to better facilitate communication.

According to another aspect of the invention, a remote expert is allowed to control cursor movements and to modify screen data. Any changes made by the remote expert to one or more display windows of the data processing system may be transferred via the communications network to be mirrored on a corresponding display of the programmer at the local site. In one embodiment, an audio signal obtained from the remote site may also be transferred to the local site. In this manner, the remote expert is better able to participate in the procedure or examination being conducted at the local site.

In one embodiment of the invention, the amount of screen data transferred between the local and remote sites is minimized by only transmitting data associated with screen updates. Portions of a screen display that are not modified are refreshed using previously-transferred data. Data encoding schemes may be employed to further reduce the size of the transfers.

Routing of the data between the local and remote sites may be performed by a hub. In one embodiment, the hub is a stand-alone unit coupling the medical, video, audio, and programming devices to the communications network. The hub implements one or more communication stacks to facilitate the routing of this information to the remote site, and routing of data from the remote site to the programmer.

In an alternative embodiment of the invention, the programmer performs data routing functions associated with the current invention. In this embodiment, the programmer is coupled directly to video, audio, and other medical devices to receive, temporarily buffer, and re-transmit the data to the communications network for transfer to the remote site.

BRIEF DESCRIPTION OF THE DRAWINGS

FIG. 11 is one embodiment of a screen display that may be provided after the pacing parameter icon is selected on either data processing system or programmer.

DETAILED DESCRIPTION OF PREFERRED EMBODIMENTS

Figure 1:
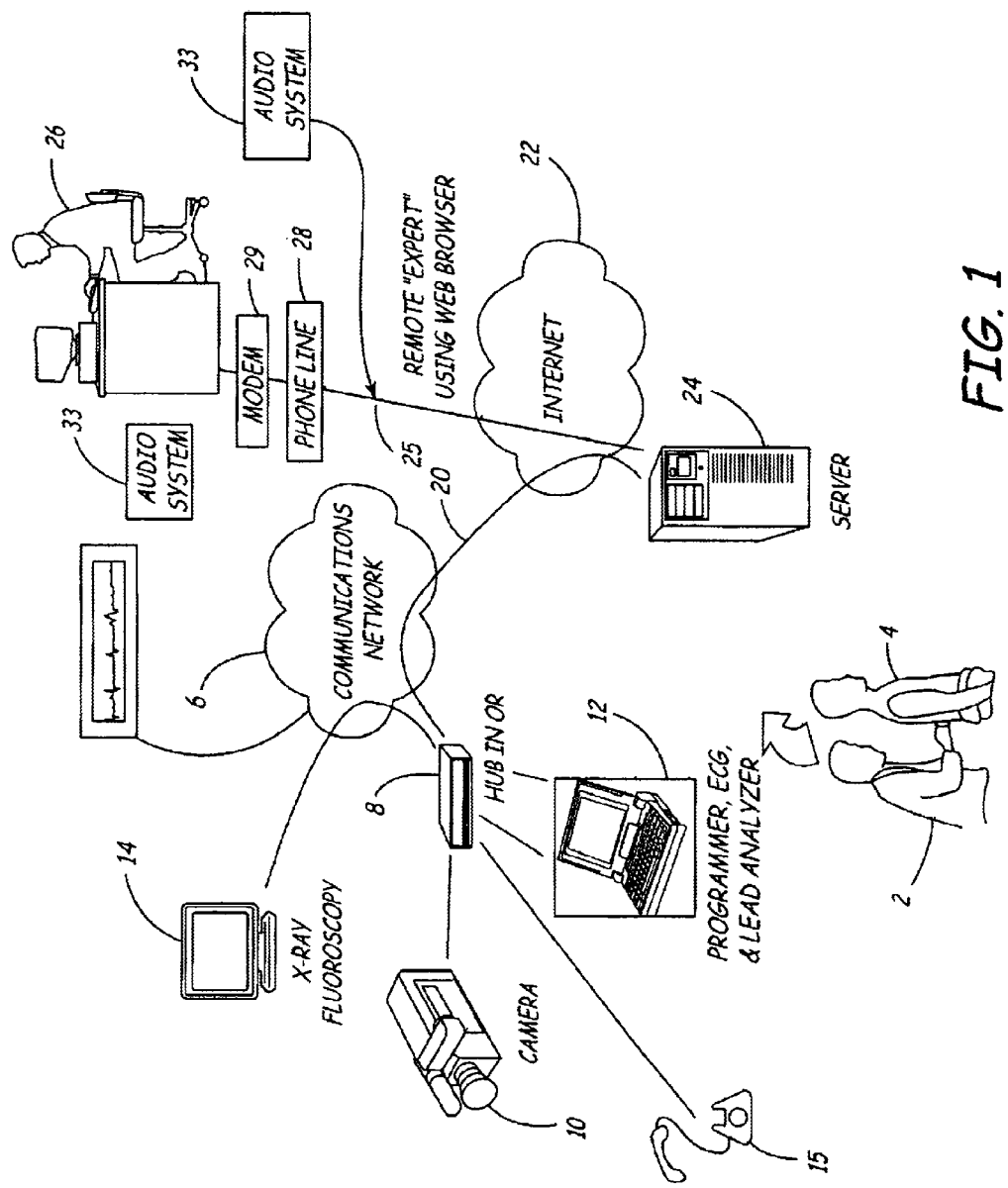
FIG. 1 is a diagram illustrating one embodiment of the present invention.

FIG. 1 is a diagram illustrating one embodiment of the present invention. A clinician 2 and patient 4 are shown at a first location, which may be a hospital or other clinic. For example, this first location could be an operating room wherein the patient is undergoing a surgical procedure such as the implantation of a medical device. The first location includes a communications network 6 which may be a Local Area Network (LAN), a Wide Area Network (WAN), or equivalent suitable communications facility.

A programmer 12 is shown coupled to the communications network 6. During an implant procedure, this type of programmer 12 is used to configure an Implantable Medical Device (IMD) to deliver a prescribed therapy. For example, a pacemaker may be programmed to deliver pacing pulses at a desired rate and signal level. The programmer may also be utilized to receive physiological signals from a patient's body. In one instance, the programmer communicates with the IMD using a communications circuit such as a telemetry device to thereby obtain physiological data such as an electrocardiogram (EGM) waveform. The programmer may display this waveform and other physiological data received from the IMD to allow the clinician to optimize the delivered therapy to meet patient needs. In one embodiment, a Model 9790 commercially available from the Medtronic Corporation may be used for this purpose, although many other types of programmers may be adapted for use with the current invention.

One or more devices located at the first location may be coupled to the communications network directly, or through some type of communications hub 8. Examples of such devices include a video camera 10 for receiving video data obtained at the first location. This video data could include a live recording of a surgical procedure, for example.

Yet other types of medical devices may interface to communications network 6. For example, an X-ray fluoroscopy system 14 may be coupled to this network. Such fluoroscopy systems are used to obtain images of fluorovisible devices and contrast media located within a patient's body. Legacy medical systems such as fluoroscopy system 14 generally transfer data as an NTCS video signal, and are adapted to interface to a video adaptor card provided by hub 8. Such signals may be transferred over various network connections that include Ethernet or infrared connections. Newer versions of medical devices such as device 14 are designed to provide a high-resolution video signal, and therefore are adapted to interface to a high resolution video adaptor that resides on hub 8. The high resolution data provided by these devices may be transferred over suitable network connections that include DICOM and the Medical Information Bus.

Many other types of medical devices are adaptable for use within the context of the current invention. For example, a device for obtaining an electrocadiograph (ECG) signal via electrodes placed externally on a patient's skin may be coupled directly to the communications network. This signal may be transferred via communications network using mechanisms similar to those described above with respect to the transfer of fluoroscopy data.

Finally, as noted above, the signal data obtained by camera 10 may include audio data such as that generated during a surgical procedure. Yet other devices 15 for transferring voice and/or other audible information may be coupled to communications network 6. This may include a telephone or some other type of speaker system.

FIG. 1 further illustrates a communication channel 20 that is coupled to communications network 6. This may be implemented using a modem, or any other type of network connection known in the art for this purpose, including Ethernet, ATM, DSL, cable modem, ISDN, infrared, or wireless connections such as Bluetooth or 802.11 are adaptable for this purpose. The particular network connection must be selected to accommodate the various types of data that will be transferred, as discussed above.

Communications channel 20 is further coupled to a second communications network 22, which may be the internet, intranet, extranet, or world-wide-web, for example. A server system 24 coupled to network 22 further provides a communication channel 25 to a remotely-located user 26. Communications channel 25 couples to a data processing system 27 such as a personal computer or a programmer in a manner known in the art. This connection may be accomplished via a phone line 28 using a modem 29. Alternatively, any other type of connection suitable for this purpose may be used, including those listed above.

Communication channels 20 transfers various types of data including graphical data, and audio information between communications network 6 and communications channel 25. Data processing system 27 is capable of providing the audio and video data to the remote user 26, who may be a physician, a company representative associated with an IMD, or some other expert. In this manner, the remote user is able to participate in the procedure occurring at the first location.

According to one aspect of the system, an image appearing on programmer 12 may be transferred in real time to the remote data processing system 27. This allows the remote expert 26 to view the various screens of programmer 12 while these screens are being displayed at the first location. Additionally, the remote expert is able to view, in substantially real-time, the cursor movements as controlled by a local user at the first site. Similarly, the remote expert 26 is allowed to control cursor movements within a display screen of the remote data processing system 27 that can be viewed on the screen of programmer 12 in substantially real time. This ability to share programmer screen data in real-time better facilitates communication between experts at two or more different locations.

According to yet another aspect of the invention, a system 33 for receiving audio data at the remote location is coupled to communications channel 25, as shown in FIG. 1. This system allows voice and/or other audio signals to be transferred from the remote expert 26 to the local clinician 2. This facilitates direct communication between personnel at the local site and the remote expert 26.

Figure 2:
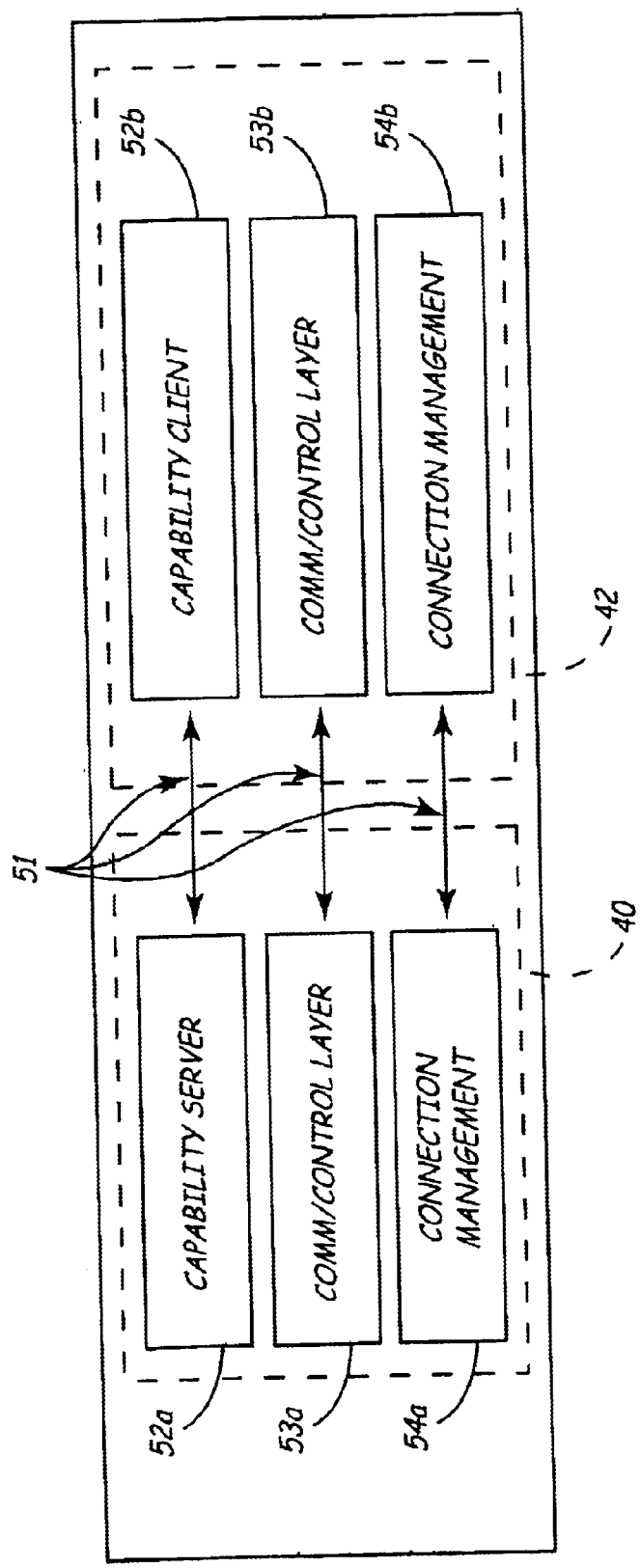
FIG. 2 is a block diagram illustrating one embodiment of the communication software needed to support the system of the current invention.

FIG. 2 is a high-level block diagram illustrating one embodiment of the communication software needed to support the system described above. Block 40 (shown dashed) represents software executing on hub 8. Block 42 (also shown dashed) represents software executing on data processing system 27. A capability server 52a, a communications control layer 53a, and connection management software 54a are executing on hub 8. These software modules communicate, respectively, with a capability client 52b, the communication control layer 53b, and the connection management software 54b executing on the data processing system 27. Similar versions of the software modules shown in block 40 may also be adapted to run on programmer 12 in a manner to be discussed below.

Figure 3:
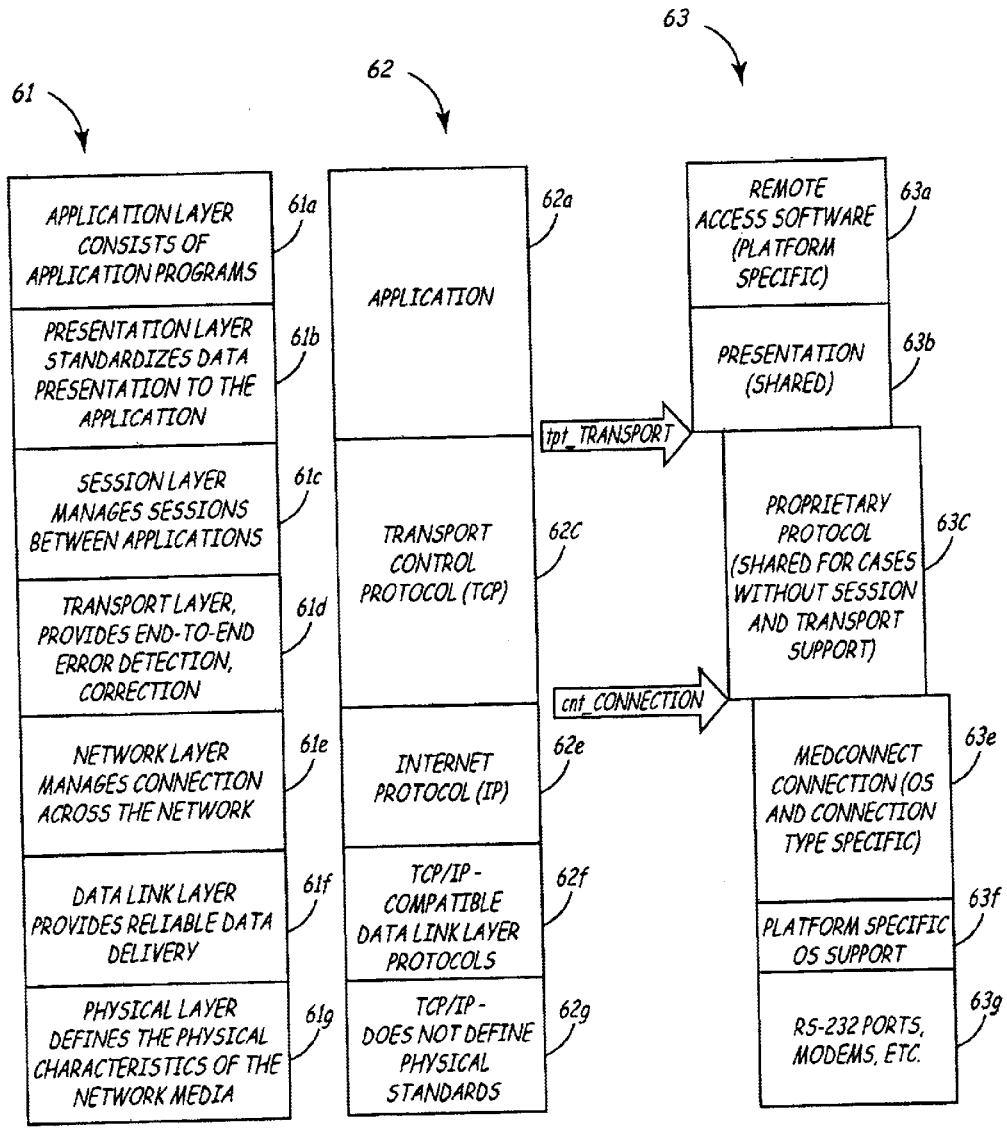
FIG. 3 is a block diagram illustrating in more detail several possible embodiments of software that support the communications system of the current invention.

FIG. 3 is a block diagram illustrating in more detail several possible embodiments of the communications software (also referred to as a "communications stack") that may be employed by the current invention. The software/firmware entities shown in column 61 comprise the seven-layer network model for supporting network communications, as is known in the art. Column 62 of FIG. 3 illustrates one manner of implementing the seven-layer protocol shown in column 61. The implementation shown in column 62 is adapted for use with internet applications. In column 62, the application program in block 62a implements both the application and presentation layers 61a and 61b, respectively. The transport control protocol (TCP) in block 62c is selected to implement the session and transport layers 61c and 61d, respectively. The internet protocol (IP) in block 62e implements the network layer shown in block 61e. Block 62f represents the data link layer, which may be any one of a number of protocols adapted for use with the TCP/IP protocols. When TCP/IP protocol is used, physical standards are not defined, as is indicated by block 62g.

The implementation of the seven-lay protocol that is illustrated in column 62 is a standard communication stack implementation that is used in many off-the-shelf applications. This standard communication stack adapted with a special application layer 62a would be used on hub 8 and data processing system 27 to handle both video data received from the camera 10, and the device data obtained from the X-ray fluoroscopy device 14 and other similar devices. In one embodiment, a streaming protocol may be substituted for the TCP layer portion of the TCP/IP layer 62f. In a manner known in the art, the communication stack is used to create packets of data having the appropriate header information identifying the source and the type of data being transferred. These data packets may then be routed to a destination device such as data processing system 27.

Column 63 of FIG. 3 illustrates yet another manner of implementing the seven-layer protocol. This implementation is particularly adapted for screen data provided by programmer 12 and data processing system 27. In this embodiment, proprietary protocols are used. This software configuration is exemplified by "Medconnect" software adapted to execute on the Medtronic 9790 programmer to support the current inventive system. In this embodiment, a remote access software application 63a is provided to support a remote communication function. This program is executed to establish communications between the host programmer and a remotely-located programmer or other system such as data processing system 27 executing compatible remote access software. Remote access software, which implements the application layer of the seven-layer protocol, interfaces with presentation software 63b, which implements the presentation layer 61b. In block 63c, a proprietary protocol may be used to implement the session and transport layers 61c and 61d, respectively. Similarly, proprietary connection software 63e and platform-specific support software 63f may be provided to be compatible with a specific operating system (OS) and connection-type specific. This connection and support software 63e and 63f are provided to implement network layer 61e. Finally, software 63g is shown provided to support specific connection devices such as RS-232 ports, modems, and etc.

Figure 4:
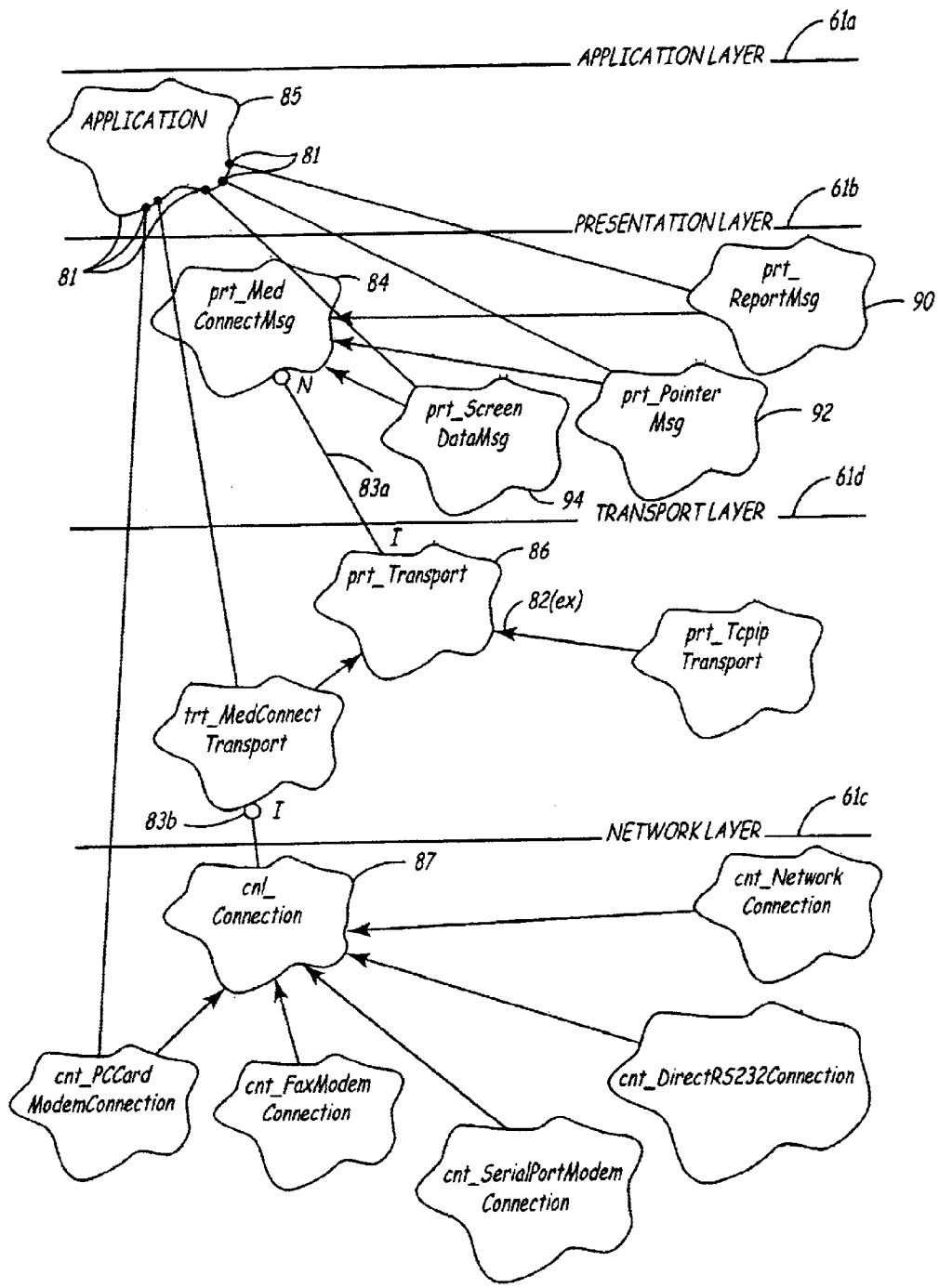
FIG. 4 is a thread diagram illustrating the communication between the software entities of FIG. 3.

FIG. 4 is a thread diagram illustrating the relationship between the software entities modeled by column 63 of FIG. 3. Software and/or firmware similar to that represented in FIG. 4 may be provided on both programmer 12 and on data processing system 27 to support transfer of the screen data. Application software 85 provides the device functionality. This may include the capability to display and analyze patient data, including physiological waveforms such as an electrocardiogram (EGM).

Control of the programmer displays may be implemented within the presentation layer 61b. In this layer, the display software 84 contains data used for location and other display functions. Communication between the application 85 and the presentation layers is accomplished via message data shown as prt_ReportMsg 90, prt_PointerMsg 92, and prt_ScreenDataMsg 94. This data is further used to format communications messages between the programmer 12 and the remote data processing system 27. These data components are of a base type prt_MedConnectMsg. All of these message types would be contained in the presentation layer 61b of FIG. 3. Each portion of data being communication may be temporarily buffered and reformatted to create data packets discussed above.

The application and presentation layers 61a and 61b are linked to the transport and network layers 61d and 61e as shown. The arrows indicate that the source software entity (that is, source of the arrow) is a subset of the target data (that is, the data at which the arrow is pointing.) For example, the software module shown as "prt_Transport" 86, which is implemented in the Transport layer 61d, relates to the functionality provided to communicate the data between the programmer 12 and the data processing system 27. This "tpt_Transport" base type equates to the block 63c of FIG. 3.

The "cnt_Connection" base type corresponds to the network layer 61e. For specialized different types of communications media, there are representations given such as base type cnt_Connection component 86, each of which uses generalized abilities of the Base type.

More details associated with the software constructs shown in FIG. 4 are provided in Appendix A. As described previously, these software constructs are particularly adapted to handle the transfer of screen data associated with the display windows provided by the programmer 12 and data processing system 27. Next, the particulars associated with this transfer of screen data are considered.

Figure 5:
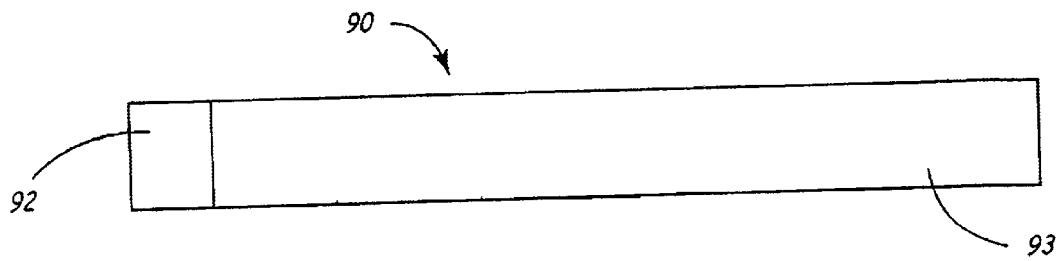
FIG. 5 is a block diagram of a display window as may be used on a programmer screen to display a physiological signal.

FIG. 5 is a block diagram of display window 90 as may be used on a programmer screen to display a physiological signal. The widow includes at least two portions, an active portion 92 and a trailing portion 93. Only a small part of window 90 is actively receiving new data at any time in either the remote or local device. For example, generally, only the leading edge of a physiological waveform is changing, with the remainder of the display reflecting previously-collected data. Therefore only the active portion 92 of the display needs to be maintained through coordination of the local and remote systems. Thus, while the local device is receiving the actual physiological waveform such as an EGM from the patient for display on the programmer screen, the local programmer 12 is also sending this data via communications channels 20 and 25 to a remote data processing system 27. The amount of data to transfer is very small since only the leading (changing) edge of the waveform needs to be sent. The refresh rate of the system will depend on the width of window 92, which is selectable based on the implementation, the baud rate for data transfer, the speed of the local computing and display device, and the resolution of the image.

By transferring only the leading edge of the physiological waveform, the amount of transferred data can be significantly reduced. Another way to reduce data associated with physiological waveform involves use of a two-tone display for that data.

Figure 6:
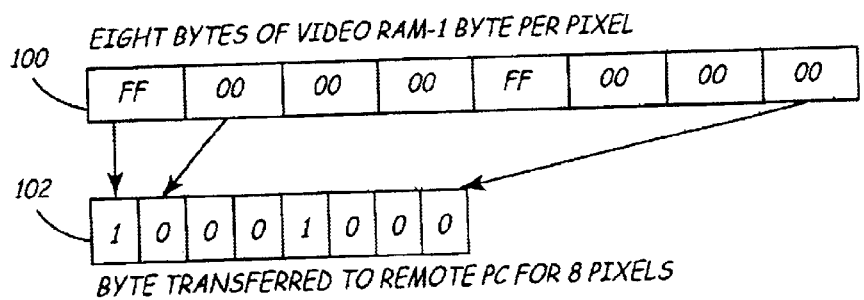
FIG. 6 is a block diagram illustrating the manner in which use of a two-tone display can significantly reduce the amount of data transferred between a local and remote screen.

FIG. 6 is a block diagram illustrating the manner in which use of a two-tone display can significantly reduce the amount of data transferred between a local and remote screen. Representation in a color display includes pixels that may be any one of eight colors, the color and other visual characteristics of each pixel is generally describe by information stored with a respective byte in memory. A larger portion of memory is required to describe a pixel included within a display that incorporates a larger array of colors. By limiting a display to a two-tone configuration including, for example, only black or white pixels, each pixel requires only a single bit of descriptive data. FIG. 6 shows the manner in which the use of a two-tone screen may be used to convert eight bytes of video data stored in memory 100 to one byte of data 102. Because of the large reduction in the amount of data that must be transferred, updates to a remote screen may be accomplished in substantially real-time using far less bandwidth than would otherwise be required. Additionally, this type of two-tone display is particularly suited for use when displaying physiological waveforms such as EGM data, since color does not serve to enhance user understanding of the data. Therefore, in one embodiment of the current invention, windows used to display physiological waveform data such as EGM information are displayed in black and white.

Another approach used to significantly reduce the size of transferred data involves dividing all, or a portion of, a screen display into predetermined screen regions. For example, the active portion 92 of window 90 may be divided into eight-by-six-pixel regions each containing 48 pixels. At predetermined time periods, physiological waveform data obtained from a patient is transformed into a visual physiological waveform within the active portion. Then it is determined which of the predetermined windows includes pixel information that has changed. Only the changed screen data is transferred to the remote site to update the screen on the data processing system 27. Other unchanged data is refreshed by data processing system 27 using the last known state of this data as stored in a storage device on that system. This greatly reduces the data transferred from one site to the next.

Figure 7:
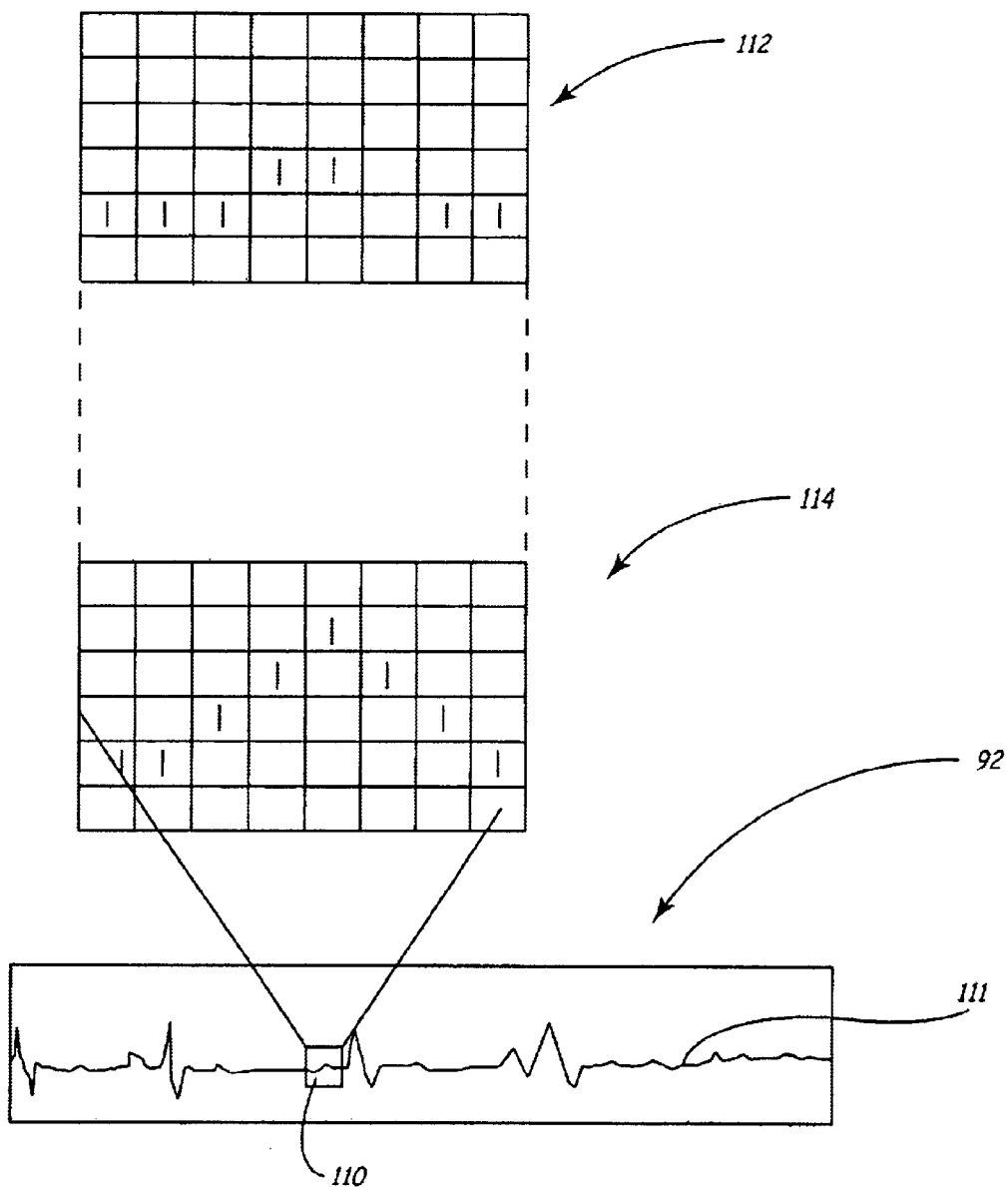
FIG. 7 illustrates the division of an active region of a window into predetermined regions that are monitored for changed data.

FIG. 7 illustrates the manner of dividing active region 92 of window 90 into predetermined regions such as region 110. Region 110 is an eight-by-six-pixel region that includes a portion of the physiological signal 111. Snap-shot 112 illustrates the state of region 110 at time T0. Similarly, snap-shot 114 illustrates the state of this region a predetermined time later at time T1. The state of some of the pixels in region 110 changes between time T0 and T1. Therefore, the pixels within region 110 are transferred to the remote data processing system 27 for display.

In one embodiment, a packet of data used to represent the waveform data includes a header section and a data section. The header section includes a bit corresponding to each of the regions in a display window, such as region 110 of FIG. 7. Each bit of the header is set to a predetermined state to indicate whether or not the corresponding region includes changed data. For example, the bit of the header representative of region 110 may be set to "one" to indicate the presence of changed data. For each region including changed data, corresponding data information appears in the data section of the transferred packet. Regions of the display that are indicated as not including changed data are not associated with data in the data portion of the packet. This significantly reduces the amount of data that must be transferred.

Figure 8:
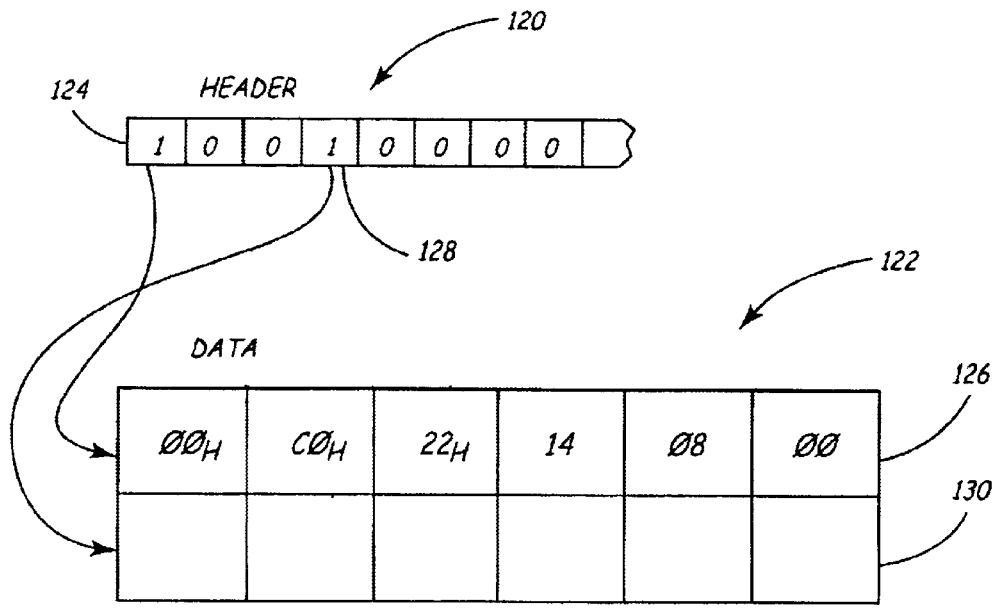
FIG. 8 is a block diagram illustrating a data packet including both header and data sections.

FIG. 8 is a block diagram illustrating a data packet including a header section 120 and a data section 122. For illustration purposes, assume that the first bit 124 in the header section corresponds to region 110 of FIG. 7. Because this bit set, it is indicated that the screen data of region 110 has changed. Therefore, the data section 122 will include corresponding data 126 describing the changed region of the screen. The corresponding data 126 is six bytes long, with one bit for each pixel in screen region 110. Assuming that each byte represents a row of the snap-shot 114 of region 110, and further assuming that the first byte of data corresponds to the bottom eight-pixels of snap-shot 114, the second byte corresponds to the adjacent eight pixels, and so on, the corresponding description of the snap-shot 114 of region 110 would appear as shown.

Other bits in the header are set to indicate additional regions of the screen that changed since the last screen update. For example, bit 128 corresponds to another changed region, and therefore is associated with six bytes of corresponding data 130 in data section 122.

In one embodiment, the location of each region of screen data such as region 110 is stored in a look-up table (e.g., using X and Y coordinates) at both the local and remote systems. This allows the transferred data as shown in FIG. 8 to be translated into a screen display.

To even further reduce the size of a transferred data packet, encoding schemes may be employed. A typical encoding scheme that may be employed in one embodiment of the invention is called run-length encoding. According to this scheme, every byte in which all bits are of the same polarity is reduced to a single bit. An additional bit is used for each byte to indicate whether the data has been encoded. Therefore, this scheme is most beneficially employed in cases wherein a significant number of bytes may be encoded. This is generally the case in situations involving physiological waveform data, since a large portion of the window displaying the waveform will be associated with the "background", and only a small portion will represent the waveform itself.

Figure 9:
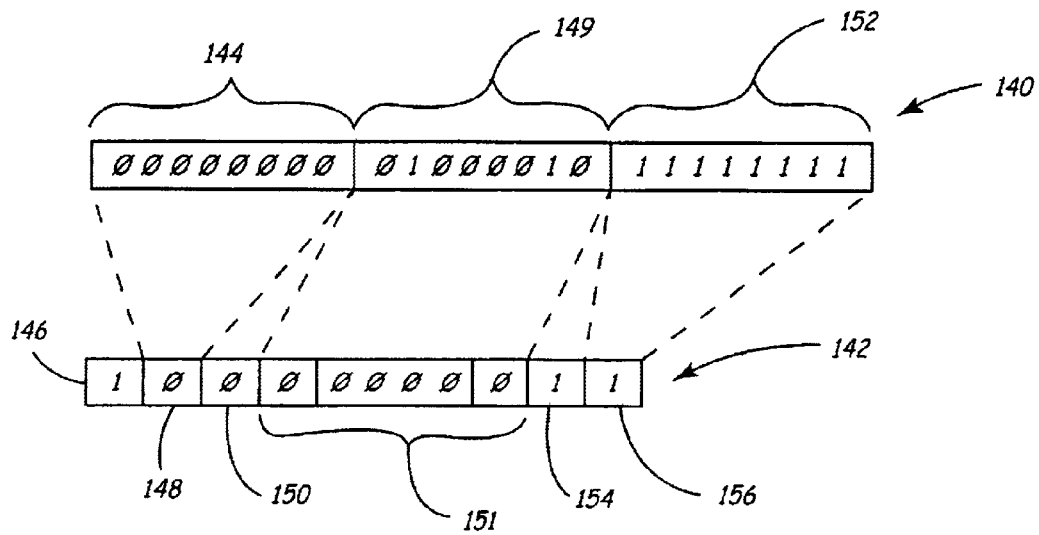
FIG. 9 illustrates the use of run-length encoding to transform three bytes of information into encoded information.

FIG. 9 illustrates the use of run-length encoding to transform three bytes of information 140 into encoded information 142. The first byte 144 includes all "zeros". Therefore, the encoded information includes a first bit 146 that is set to indicate the corresponding byte is encoded. A second bit 148 that is set to "zero" indicates all bits in the original byte of data 144 are set to zero. The next byte 149 of the original data includes both "ones" and "zeros" and therefore is not encoded. Bit 150 is cleared to indicate that encoding was not used to describe the corresponding byte of data, which is provided in the following eight bits 151. Finally, original byte 152 of data includes all "ones" and can be encoded. Bit 154 is set to indicate encoding is used, and the following bit 156 is set to indicate that all bits of original data are set to "one".

Many alternative types of encoding may be used instead of run-bit encoding to reduce the amount of data transferred from a local system to a remote system.

As discussed above, in one embodiment of the invention, a pointer or cursor may be moved within the programmer screen of programmer 12. This cursor movement will appear on the corresponding display screen of data processing system 27. Similarly, the remote expert 26 may control the same, or a different, cursor on the screen of data processing system 27, and such cursor movements will be displayed at the local site on the screen of programmer 12.

In one embodiment, information related to cursor movement is transferred separately from the physiological waveform and/or other screen data. The transferred information therefore includes a packet description of the screen data, including any physiological waveform data, and a separate packet indicating the location of the pointer or cursor. According to one aspect of the invention, cursor data may be selectively enabled or disabled at the programmer 12 and/or the remote data processing system 27 to allow the waveform data to be better analyzed.

In one embodiment of the invention, the cursor movement may be controlled by a person at the local site interacting with programmer 12, and may also be controlled by the remote expert. In this embodiment, either the clinician 2 or the remote expert 26, but not both, are allowed to move the cursor at once. If two conflicting cursor movement requests are made simultaneously, the request received from a predetermined one of the systems will take precedence. For example, it may be determined upon system initialization that the programmer 12 will take precedence when two conflicting cursor movement requests are received simultaneously.

In another embodiment of the invention, both the local and remote operators of programmer 12 and data processing system 27 have control over separate cursors. In this embodiment, both the local and remote experts may simultaneously move respective cursors.

According to one aspect of the current invention, a person at the local site interfacing to programmer 12 has control over the screens being displayed by the programmer. This control is facilitated via a user interface that may include a keyboard, a touch screen, a mouse, and other interface devices known in the art. As the various screens are displayed, the control sequences provided by the local user may be transferred over communications channels 20 and 25 in a special data packet. These control sequences are interpreted by a program executing on data processing system 27 so that similar, or the same, screens are displayed by data processing system 27. Thus, the remote expert is allowed to view, in substantially real-time, the screen displays appearing on the programmer 12.

Figure 10:
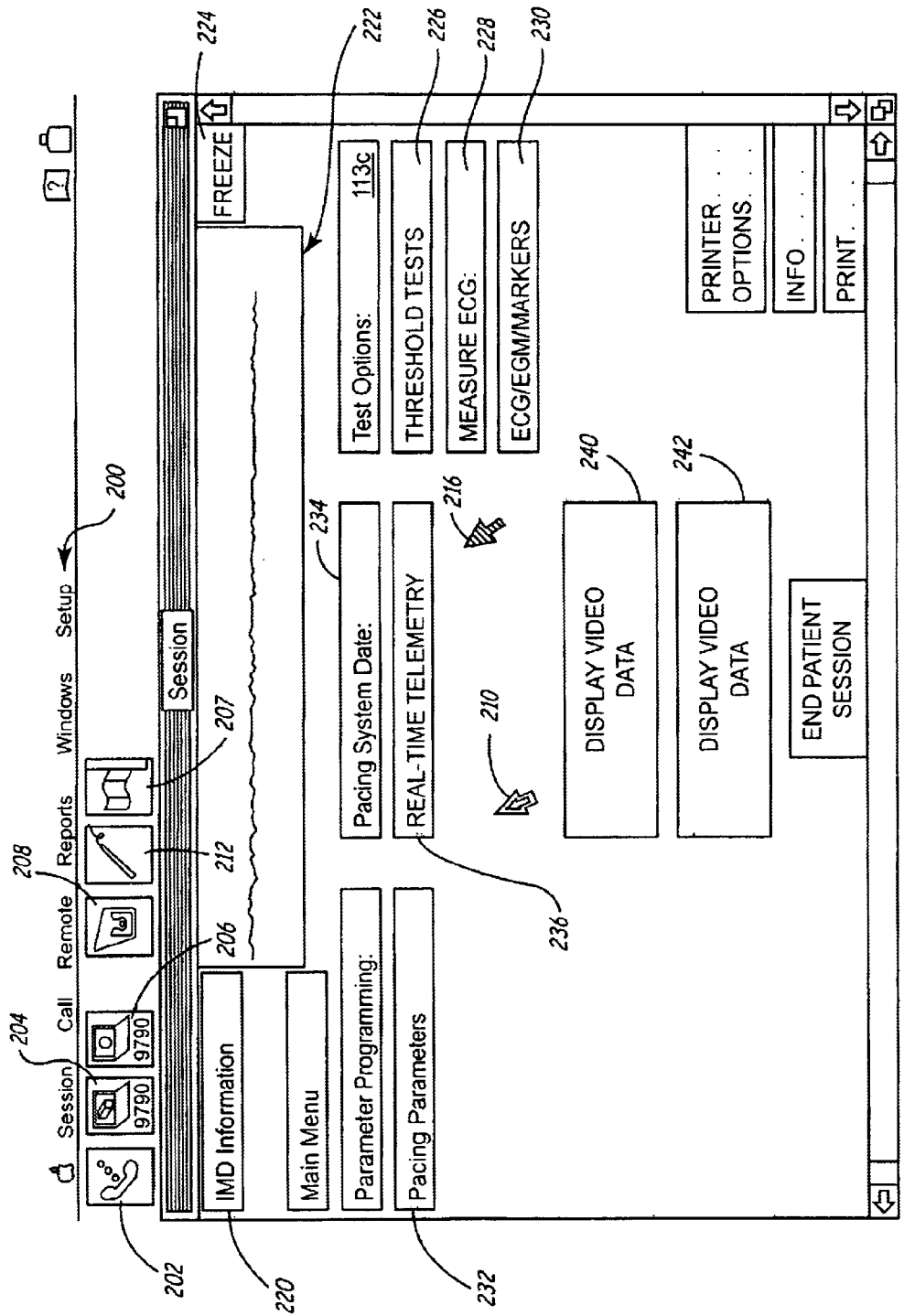
FIG. 10 is an example of a display window that may be displayed by programmer and by data processing system.

FIG. 10 is an example of a display window that may be displayed by programmer 12 and by data processing system 27. In a manner known in the art, window includes a toolbar 200. This toolbar includes multiple icons for invoking various functions. For example, icon 202 may be used to access a phone directory when activated by a cursor. Selection of a phone number from the directory may then allow interaction with a communications program to invoke session with a remote system. Icons 204 and 206 may provide indications of how often the updates occur between the remote and local screen displays during this session, and can be used to change the frequency of the updates in one embodiment of the invention. Icon 207 may be utilized to print various screens displays.

In one embodiment, cursor control functions may be provided. For example, icon 208 may be provided to enable a cursor such as cursor 210 to be controlled by the clinician 2. As described above, in this instance, cursor movements controlled by the clinician 2 or other expert located at the patient site will also appear on the screen display of the data processing system 27 for viewing by the remote expert 26. In one embodiment, control of the cursor is shared with the remote expert 26. In this embodiment, activation by the clinician of icon 212 then allows the remote expert to control the cursor movements. In this mode, the clinician 2 no longer has control of over the cursor.

It may be noted that since the screen shown in FIG. 10 is provided on both programmer 12 and data processing system 27, conflicting requests may be entered by the local and remote experts. For example, both the local and remote experts may use the icons of toolbar 200 in attempt to gain control over cursor movements. To resolve such conflicts, preferably one system may be selected as the master such that the request made on the master system takes precedence over the other conflicting request. For example, the programmer 12 may be selected as the master to allow requests made by the clinician 2 to override similar conflicting requests made by the remote expert 26.

In an alternative embodiment of the invention, a second cursor 216 is provided. Each of the cursors 210 and 216 may be dedicated to a respective one of the local and remote experts so that cursor control need not be shared. The cursors may be represented uniquely on the screen so that confusion does not result from the simultaneous manipulation of the cursors on the display screen. These cursors may be used to point to aspects of the physiological signal in window 222 and/or to activate functions provided by the display as discussed herein.

In one embodiment, cursor 216 only appears on the data processing system 27, not on the local programmer 12. In this embodiment, cursor 216 is used by the remote expert 26 to perform auxiliary tasks in background such as consulting an expert system resident on data processing system 27.

Other functions are shown being provided on the screen of FIG. 10. For example, window 220 may display information associated with the implanted medical device (IMD) in communication with programmer 12. For instance, this window may provide the model number, serial number and/or other unique identifier information. Window 222 is provided to illustrate a physiological waveform being monitored at the patient site. For example, this window may provide an EGM or ECG signal in the manner discussed above. Icon 224 may be selected to freeze the display in window 222 so that the physiological signal may be further analyzed or saved in memory. If no physiological data is being monitored, window 222 does not include a display.

Other options associated with the physiological waveform data may be provided as by icons 226, 228, and 230. For example, threshold tests may be invoked by selecting icon 226. Selection of icon 228 initiates the display of the ECG waveform data if such data is available. Other types of physiological waveform data may be collected simultaneously from a patient, and in this case, other icons may be provided to select the data being displayed in window 222. Icon 230 is provided to allow markers to be included in window 222 in a manner known in the art.

Icons associated with the configuration of an implantable medical device may also be provided by the display screen. For example, selection of icon 232 may allow a remote expert 26 to open a display that includes operating parameters for an IMD. In one embodiment, the remote expert 26 may further be allowed to change the IMD configuration via this display. To do this, the remote expert may be required to supply a password, for instance. Other data associated with the IMD operation or setup may be viewed by selecting icon 234. An additional icon 236 may be provided to view and/or modify the configuration of the IMD communication system, which may include a telemetry circuit.

Also provided by the current invention is a mechanism for selecting the display of video data obtained by camera 10. As discussed above in reference to FIG. 1, display camera 10 is provided to record events occurring at the patient's location, which may be a hospital. These events may include the implantation and/or programming of an IMD. The recorded video data may be in black and white or, preferably, in color, and may include an audio signal from the local site. The transfer of this video information is discussed further below. In one embodiment of the invention, the remote expert 26 is allowed to view the video data by selecting icon 240, which opens an additional window that may occupy some, or all of, the display screen of the data processing system 27. The user may toggle between a video display and the screen data shown in FIG. 10, or may overlay these windows such that they are simultaneously displayed. Icon selection and/or key stroke sequences may be utilized to select the manner in which the window(s) are displayed, as is known in the art. In one embodiment, selection of icon 240 when video data is not available results in the display of a message indicating the unavailability of such data. Alternatively, a blank screen may be displayed in the absence of a video signal.

Another icon similar to icon 240 may be provided to display device data such as data obtained from X-ray fluoroscopy device 14. Selection of icon 242, for example, may activate yet another window containing the fluoroscopy image obtained by device 14, which may be displayed in substantially real-time. As discussed above with respect to the window containing video data, the device data window may be selected and enlarged to occupy the entire display screen of data processing system 27. In this configuration, user input such as keystrokes is required to toggle between the various active windows. Alternatively, one or more additional windows may be selected to reside on the display screen at once. In one embodiment of the invention, the user is allowed to select the manner in which the windows are arranged on the screen.

Figure 11:
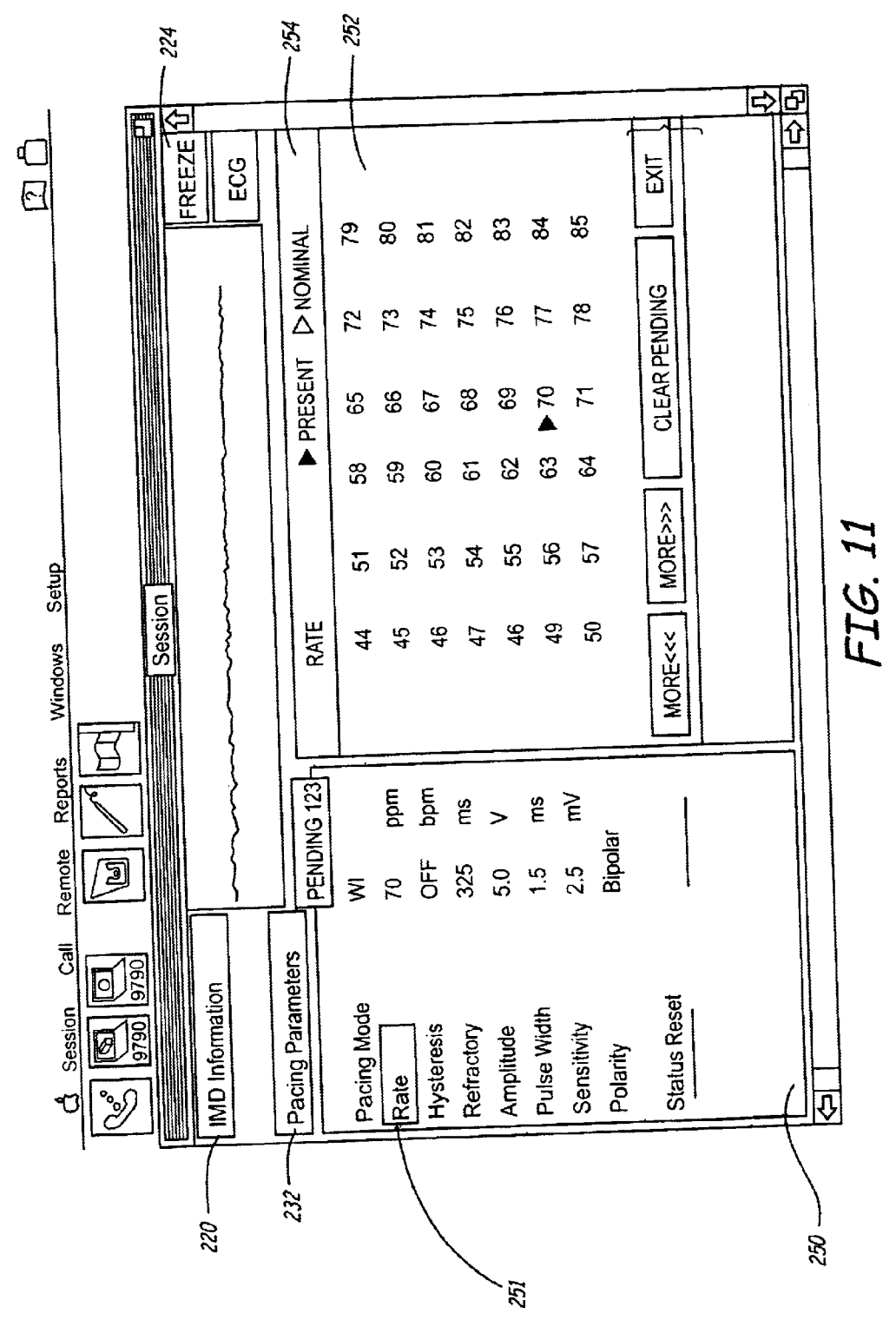

FIG. 11 is one embodiment of a screen display that may be provided after the pacing parameters icon 232 is selected on either data processing system 27 or programmer 12. Various pacing parameters are indicated in the display window 250. According to one manner of modifying the configuration, a cursor may be used to select one of the parameters such as "rate", which is then highlighted in the manner shown by block 251. Once the parameter is highlighted, the allowable setting for that parameter is indicating in display window 252. "Present" and/or "Nominal" values for the parameter may also be indicated in display window as shown. The expert may then modify the parameter value by selecting a new value from the window 252. This may be accomplished using a touch screen, a keyboard, a mouse, or any other input mechanism known in the art. In another embodiment, the configuration may be modified using keystrokes to toggle between the allowable settings for a selected parameter.

As discussed above, the modification of parameters by remote expert 26 may be contingent upon the expert supplying a password or having an appropriate privilege access level. In another embodiment, the display screen does not allow the remote expert to modify parameters, and any information provided by the remote expert 26 to the clinician 2 must be provided via a telephone line, for example. The clinician 2 is then required to make the changes using programmer 12. The remote expert may view these changes on data processing system 27 to verify that the configuration was modified correctly.

It may be noted that any of the functions associated with the current invention may be restricted to use at one or the other locations. For example, patient-specific data that may be viewed by selecting icon 234 may be considered confidential. If desired, the selection of icon 234 to view this data may be allowed only at the local site. The remote expert may be prevented from using this function. As another example, it may be desirable to only allow the remote expert to modify certain pacing parameters. Access software executing on programmer 12 would therefore prevent local expert 2 from modifying certain parameters associated with the IMD under certain predetermined circumstances.

It may further be noted that any of the screens associated with the current invention may be updated in a manner similar to that described above with respect to the physiological waveform data. That is, preferably, only data that has been modified is transferred between the local and remote systems. Other unmodified data is stored at both the local and remote sites and used to refresh the unchanged portions of the screen displays. Cursor information is also handled in a similar manner. That is, the position of a cursor is only transferred when the associated user input indicates a change in the cursor position.

Figure 12:
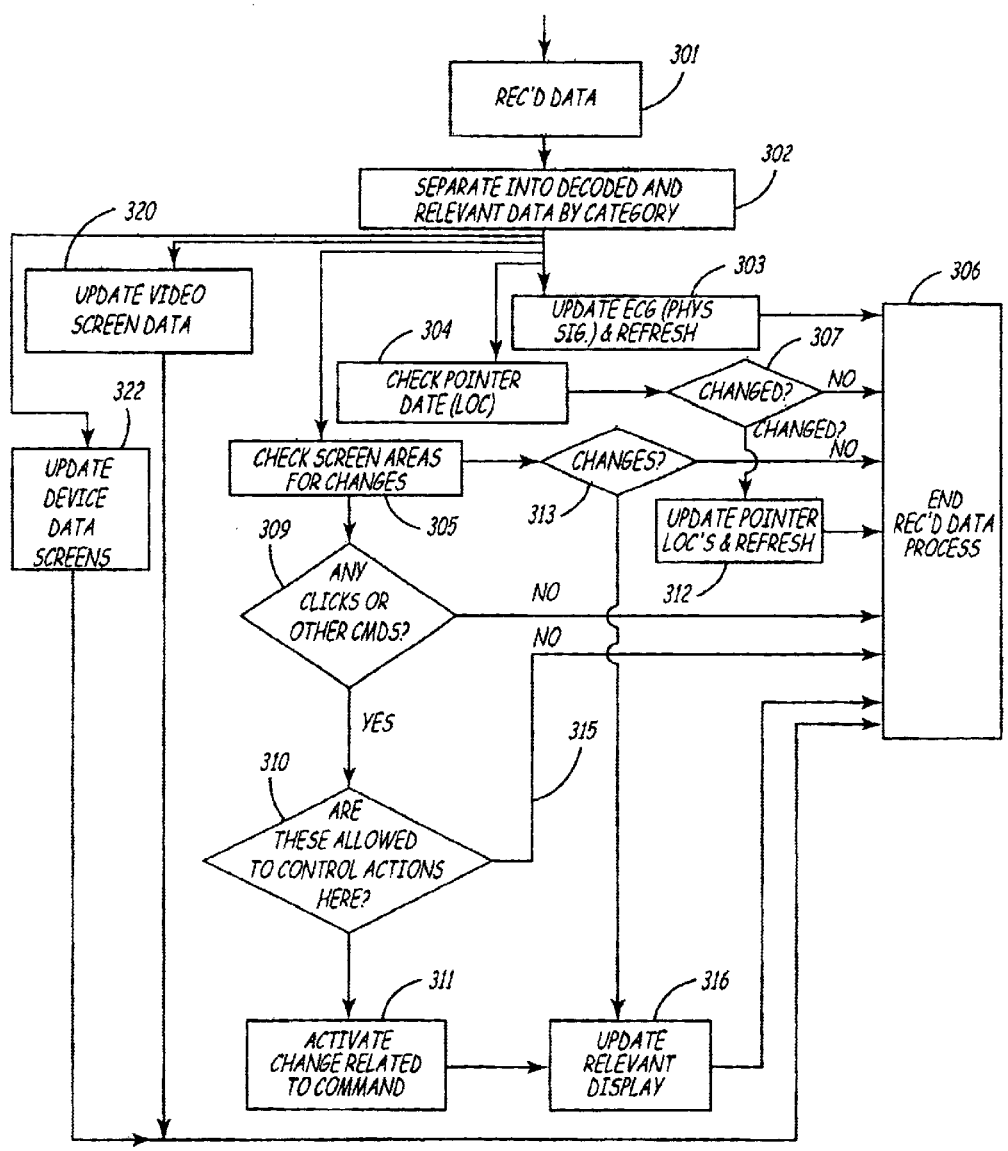
FIG. 12 is a flowchart illustrating operations occurring on the remote data processing system when receiving data from the programmer.

FIG. 12 is a flowchart illustrating operations occurring on the remote data processing system 37 when it is receiving data from programmer 12. Some similar mechanisms may be employed when the programmer is receiving data from the data processing system. In block 301, a packet of data is received by data processing system.

Next, in block 302, a header associated with the data is decoded by data processing system 27. This header, which is constructed by the communication stack software and firmware discussed above with respect to FIG. 3, is provided with the data to indicate the type and size of the data packet associated with the transfer. For example, the data transfer may include physiological signal data such as an EGM waveform that is being displayed by programmer 12. Alternatively, the data transfer may provide screen data and/or cursor information from one of the display windows of programmer 12, a stream of video data from camera 10, or data received from another monitoring device such as X-ray fluoroscopy device 14 or any other type of medical device.

Next, the transferred data processed. Physiological signal data such as EGM or ECG data may be used to update a display window such as window 222 (FIG. 10), as shown in FIG. 303. In a manner discussed above, this signal data may be limited to the changed portion of the waveform data to minimize transfer time and limit the amount of bandwidth used on the communications networks. Data associated with cursor positioning is checked to determine whether cursor movement has occurred in decision block 307. If so, the cursor location is updated in block 312.

Additionally, video data such as that received from camera 10 (FIG. 1) may be used to update a video display window, as shown in block 320. This video data may be associated with audio data in a manner known in the art. In one embodiment, the audio data is available to the remote expert when the associated video window is open. Similarly, one or more screens associated with device data such as X-ray fluoroscopy device 14 (FIG. 1) may also be updated, as shown in block 322.

Other information such as programmer screen data may be transferred to the remote system. This screen information is shown received in block 305. In one embodiment of the invention, preferably, only modified screen information is transferred to the user in the manner discussed above. It may be noted that such modifications may include control sequences that open or close windows, perform control functions such as printing display screens, reading information from an input device, or any other type of control operation supported by programmer 12. In one embodiment, these control operations cause an associated event to occur on both the programmer 12 and the data processing system 27. In this manner, the remote expert 26 may be allowed to view the operations exactly as they are occurring at the local site assuming none of the operations and/or associated data is considered confidential. This is useful if the remote expert 26 is, for example, a representative that is advising on optimal use of programmer 12 and/or on the appropriate programming parameters to be used in programming of an IMD.

Decision block 309 checks for the presence of screen control information, and if located, determines in block 310 whether the control information may be used to change the display screens of the data processing system 27. Consistent with one embodiment of the invention discussed above, privileged information such as patient data may be prevented from being displayed on data processing system 27. It may be undesirable to allow other similar types of operations to be mirrored on the remote system. In these instances, the associated control information is blocked by the remote data processing system, as shown by arrow 315. However, if the control information is not associated with a privilege operation, the related commands are activated and the display is updated. This shown in blocks 311 and 316. If the updated screen data is not associated with control information, the screen is updated in the specified manner, as shown in decision block 313 and block 316.

As discussed above, a process similar to that shown in FIG. 11 may be used to update the screens of programmer 12 using data received from data processing system 27. In this manner, a remote expert 26 may demonstrate, for example, a new feature associated with programmer 12 without actually being present at the local site. As another example of remote participation in a clinical procedure, the remote expert may be a physician participating in a surgical procedure from a remote location. In response to physiological waveform data or video data provided by camera 10, either or both of which may be viewed on a window of data processing system 27, the remote physician may utilize the various programming screens to suggest a modification to the configuration of an IMD. This ability to share information in substantially real-time allows a remote expert to participate in clinical procedures without having to be present at the location of the patient.

Figure 13:
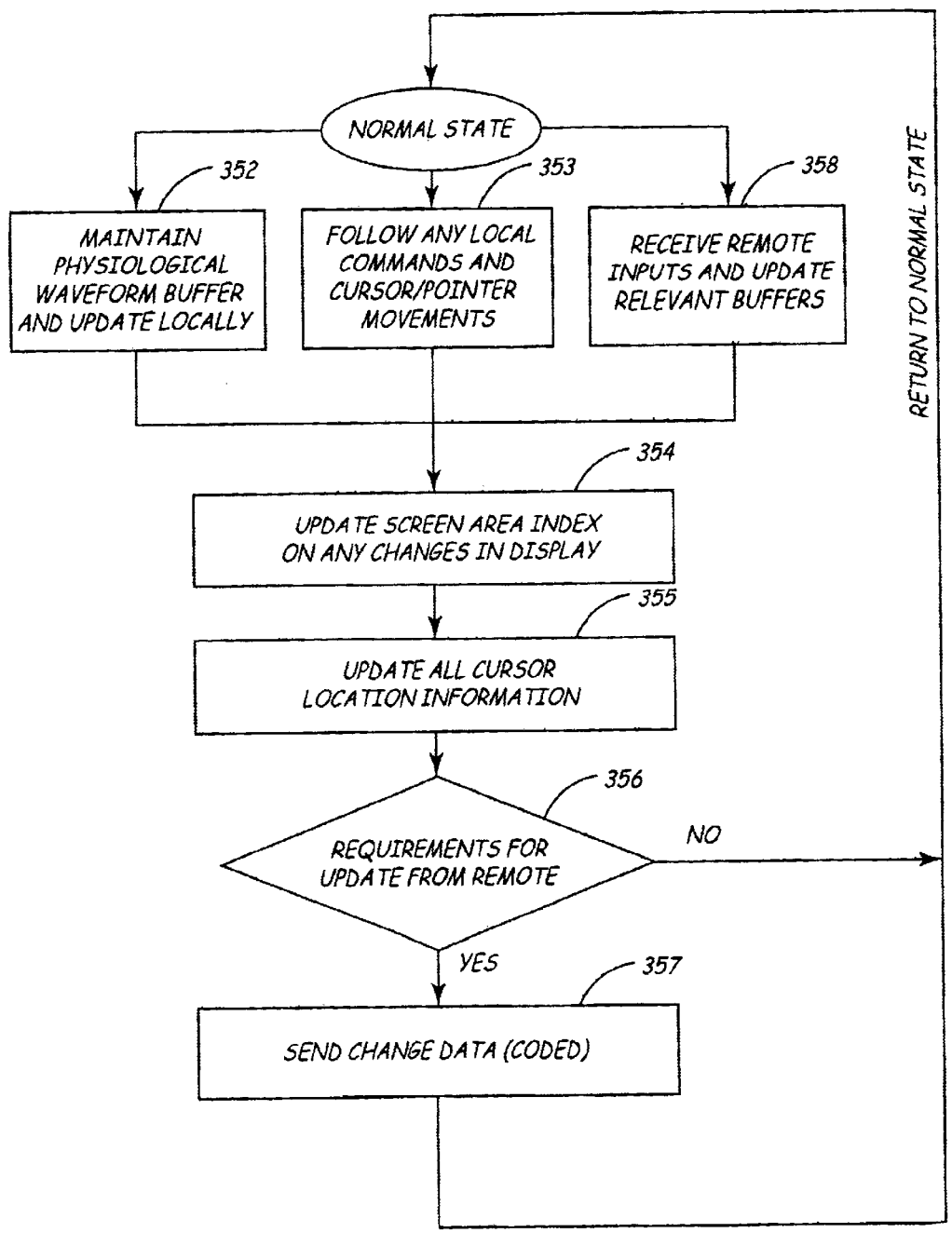
FIG. 13 is a flowchart indicating programming sequences that may be occurring on the local system during the operation of the current invention.

FIG. 13 is a flowchart representing programming sequences that may be occurring on the local system during the operation of the current inventive system. One or more physiological waveforms may be received by the programmer so that waveform data may be displayed, as shown in block 352. Any local commands initiated by icon activation or cursor movements are executed in block 353. Data indicating screen updates occurring on the remote data processing system 27 may be received and stored in associated buffers, as shown in block 358. All of this data may be used to update the associated windows of programmer 12, as shown in block 354. Updated cursor information received from the data processing system is overlaid over screen data, as shown in block 355. The display of cursor information may be disabled entirely if desired, so that screen data may be better analyzed.

Next, if changes on the local screen have occurred, data packets containing the modified data may be prepared for transfer to data processing system 27 via the communications stack discussed above in reference to FIG. 3. This is shown in blocks 356 and 357. Preparation of the data packets includes generation of the header information, and may also include encoding the data to reduce the amount of data that is transferred. In one embodiment of the invention, the local system filters data and operations that are privileged or otherwise not intended for use by the remote system. This further reduces the amount of data transferred.

It may be noted that with respect to the data transfers represented in FIG. 13, the transport and networking protocol layers of the communication stack, 61d and 61e, respectively (FIG. 3), handle channeling video, screen, and other device data into discrete channels. These layers also handle the arbitration and buffering functions associated with the data transfers. This allows multiple windows to be supported by data processing system simultaneously in the manner discussed above.

Figure 14:
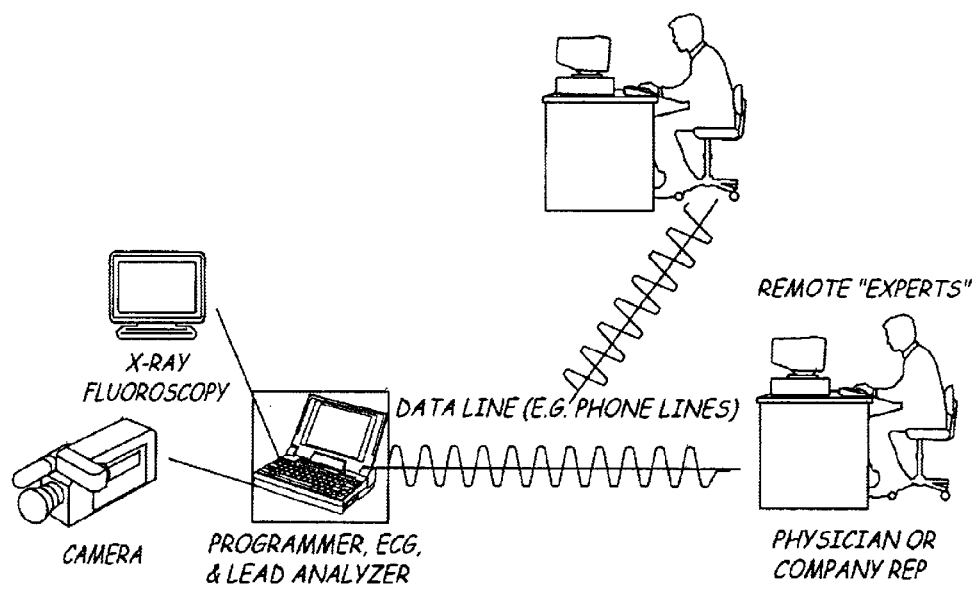
FIG. 14 is another embodiment of the current invention, wherein a programmer 12 routes all data from a local site to a remote user.

FIG. 14 is another embodiment of the current invention, wherein a programmer 12 routes all data from a local site to a remote user. In this embodiment, programmer 12 includes ports to receive data from video camera 10. Programmer 12 may also receive data from other devices such as X-ray fluoroscopy device 14, and/or any of the other medical devices discussed above. In this embodiment, hub 8 and communication network 6 (FIG. 1) are not utilized. Instead, the communications stack for receiving the video data and device data as shown in column 62 of FIG. 3 is implemented on the programmer 12. All data is provided over a communication channel 400 that is coupled directly to programmer 12.

Although the foregoing discussion has focused on the transfer of data to only a single remote expert, it will be appreciated that any of the foregoing embodiments may be utilized to transfer data substantially simultaneously to multiple remote locations in the manner discussed above. For example, FIG. 14 illustrates a second remote expert receiving the transferred data. Similarly, a single remote expert could be receiving data from multiple sites at substantially the same time. For example, the remote expert could be receiving video, audio, and fluoroscopy data from a hospital during an implant procedure, and could further be receiving archived patient data from a database located at a second site.

From the foregoing description and the accompanying drawings, it will be apparent to those skilled in the art that many adaptations of the current invention are possible within the scope of the current invention, which is therefore only to be limited by the following claims.

P7002.03 CIP1                                                PATENT

27

******************APPENDIX A******************

/* These three code fragments have been excerpted from actual code
files. They are presented here to illustrate a preferred embodiment
Screen Capture processing procedure for finding changed areas of screens and
allowing for compression of video RAM data which can then be sent to a remote
location without loss of waveform fidelity*/

/* Main screen processing loop */

```
void
mnt_ScreenTransfer::threadFn()
{
  NG_TRACE_FUNCTION();

unsigned int   index;
  int            minx, maxx, miny, maxy;
  int            new_minx, new_maxx, new_maxy;
  int            x, y;
  unsigned int   checked;
  bool           doneCheckingScreenWorth;
  unsigned int   lastLeftOffIndex = 0;
  prt_ScreenInfo* p_screenInfo;
  DATETIME       dt;
  mnt_Ulong      byte_length;

/******** debug collection *********/
  /* open a file for debug collection */
  if (v_debugOn) { p_v_ScreenFile = fopen("SCREEN.DAT", "w");
```

P7002.03 CIP1                                                          PATENT

28

```
        fclose(p_v_ScreenFile);           /* discard contents */
        p_v_ScreenFile = fopen("SCREEN.DAT", "w");

}
    /****** end debug collection *******/ try
    {
      // printf("The ScrnThread is executing.\n");
      p_screenInfo = new prt_ScreenInfo;

v_screenThreadIsActive = TRUE;
      //tbd add to main the call to declare time-to-become-inactive while(v_screenThreadIsActive)
      {
        doneCheckingScreenWorth = FALSE;
        DosSleep(500L);

// Check to see if there is a change in environment
        // For example, maybe color was turned off
        checkEnvironment();

screenCapture();
        screenCompare();

/********** debug collection ****************/
        if (v_debugOn) {
          // %4d means 4 places of decimal, %2x means 2 places of hex, % means an output
          // Note to output that a screen capture/compare was done
```

P7002.03 CIP1                                                              PATENT

29

```
       fprintf(p_v_ScreenFile, "%.2d:%.2d:%.2d.%.2d screen capture/compare\n",
              dt.hours, dt.minutes, dt.seconds, dt.hundredths);
       fflush(p_v_ScreenFile);

5     // In order that debug file does not grow indefinitely, close after
       // two minutes of collection.
       DosGetDateTime(&dt);              // Get Date & Time
       if ( (dt.minutes - v_dateTime.minutes) > 2) {
         fflush(p_v_ScreenFile);
10       fclose(p_v_ScreenFile);
         v_debugOn = FALSE;
       }
    }
    /***********DEBUG CODE COLLECT END *************/

15  // Find Rectangles and send
    while (!doneCheckingScreenWorth)
    {

20     index = lastLeftOffIndex;
       y = index / v_bytesPerRow;
       x = index - (y * v_bytesPerRow);

minx = -1;
25
       for (checked = 0;checked < v_screenSizeInBytes;checked++)
       {
         // Check flags until we have a rectangle to send.
         if (v_screenChangedFlagBuffer[index])
30       {
           // If we don't have a rectangle yet set one.
```

P7002.03 CIP1                                                                                           PATENT

```
                                      30
                    if (minx == -1)
                    {
                        minx = maxx = x;
                        miny = maxy = y;
                    }
                    else
                    {
                        // Check the x and y gap spacing to see if we can include
                        // this in the current recatangle.
                        if ((x >= minx - v_gapAllowedX) &&
                            (x <= maxx + v_gapAllowedX) &&
                            (y >= miny - v_gapAllowedY) &&
                            (y <= maxy + v_gapAllowedY))
                        {
                            // Determine the size of the new proposed rectangle.
                            // We will not set this as the current rectangle
                            // until we know that the area is not too large
                            // for a single message.
                            new_minx = minx;
                            new_maxx = maxx;
                            new_maxy = maxy;
                            if (x < new_minx)
                            {
                                new_minx = x;
                            }
                            else if (x > new_maxx)
                            {
                                new_maxx = x;
                            }

// Since we are advancing in the y direction and we don't
```

P7002.03 CIP1                                                                PATENT

31
                    // allow wrapped rectangles.  We only need to adjust maxy.
                    if (y > new_maxy)
                    {
                        new_maxy = y;
                    }

// Is the proposed block too big for a single message?
                    // Note that following doesn't work if right side set to less than
            max
                    if (((new_maxy - miny + 1) * (new_maxx - new_minx + 1)) >
            v_maxSingleMessageSize)
                    {
                        /******* debug collection **************/
                        if (v_debugOn) {
                            /* %4d means 4 places of decimal, %2x means 2 places of
            hex, % means an output */
                            fprintf(p_v_ScreenFile,"        block-too-big test,
            %6d<=index%5dx%5dy\n",
                                index, x, y);
                            fflush(p_v_ScreenFile);
                        }
                        /***********DEBUG CODE COLLECT END
            *************/

// Send the current block, and set an index
                        // to remember where we left off.
                        lastLeftOffIndex = index;
                        break;
                    }
                    else
                    {

P7002.03 CIP1                                                            PATENT

```
                              32
                   // Make the current block equal to the proposed block.
                   minx = new_minx;
                   maxx = new_maxx;
                   maxy = new_maxy;
 5                 }
                }
                else
                {
                   // If we went too far in the y direction,
10                 // send the current block, and look for the next
                   // block where we left off.
                   if (y > maxy + v_gapAllowedY)
                   {
                      /********* debug collection ***************/
15                    if (v_debugOn) {
                      /* %4d means 4 places of decimal, %2x means 2 places of hex,
% means an output */
                         fprintf(p_v_ScreenFile,"         gap test\n");
                         fflush(p_v_ScreenFile);
20                    }
                      /***********DEBUG CODE COLLECT END
*************/ lastLeftOffIndex = index;
25                    break;
                   }
                  }
                 }
                }
30
                // Advance to the next coordinate.
```

```
                                33
            x++;
            if (x >= v_bytesPerRow)
            {
                x = 0;
                y++;
                if (y >= v_maxScreenPixelsY)
                {
                    y = 0;
                }
            }

// Need to wrap back to the beginning?
            index++;
            if (index >= v_screenSizeInBytes)
            {
                /******* debug collection **************/
                if (v_debugOn) {
                    /* %4d means 4 places of decimal, %2x means 2 places of hex, % means an output */
                    fprintf(p_v_ScreenFile,"        doneScreenWorth/wrap test\n");
                    fflush(p_v_ScreenFile);
                }

/************DEBUG CODE COLLECT END *************/
                // Added
                doneCheckingScreenWorth = TRUE;
                index = 0;

// If we found some changes, send that area. Otherwise,
                // setting index=0 leads to looking for more changes
                //at the top of the screen.
```

P7002.03 CIP1                                                                    PATENT 34
                    if (minx != -1)
                    {
                       lastLeftOffIndex = index;
                       break;
5                   }
                  }

} // end "for" checking all up to v_screenSizeInBytes

10          /******* "break" statements on "for" above end up here
            ****************************************/
                // Did we find a rectangle?...indicated by minx not being -1
                if (minx != -1)
                {
15                  byte_length = getScreenRect(minx * v_pixelsPerByte,
                                   miny,
                                   (maxx + 1)*v_pixelsPerByte-1,
                                   maxy);

20                  p_screenInfo->header.x1 = minx * v_pixelsPerByte;
                    p_screenInfo->header.y1 = miny;
                    p_screenInfo->header.x2 = (maxx + 1)*v_pixelsPerByte-1;
                    p_screenInfo->header.y2 = maxy;
                    p_screenInfo->header.skip = 0;// number of horizontal lines that are
25          skipped between each line
                    p_screenInfo->header.format = v_colorFormat;
                    p_screenInfo->header.compression = prc_comp_rlCompression;
                    // Set pointer to rectangle data.
                    p_screenInfo->p_data = v_sendRectangleBuffer;

30
                    /******** debug collection **************/

P7002.03 CIP1                                                    PATENT

35

```
        if (v_debugOn) {
            /* %4d means 4 places of decimal, %2x means 2 places of hex, %
means an output */
            DosGetDateTime(&dt);          // Get Date & Time
            fprintf(p_v_ScreenFile, "%.2d:%.2d:%.2d.%.2d ",
                dt.hours, dt.minutes, dt.seconds, dt.hundredths);
            fprintf(p_v_ScreenFile,"sending
Index=>%7dlength=>%5d%6d%6d%6d%6d \n",
                lastLeftOffIndex, byte_length, minx, maxx, miny, maxy);
            fflush(p_v_ScreenFile);
        }
        /************DEBUG CODE COLLECT END **************/

// Send the current screen rectangle.
        // For now ignoring the return from sendScreenData call
        v_p_screenDataMsg->sendScreenData(p_screenInfo, v_pixelsPerByte);

} // end if we found a rectangle (i.e. minx != -1)
    } // end while notDoneCheckingScreen's Worth
  } // end while screenThreadActive delete p_screenInfo;

// printf("The ScrnThread is exiting.\n");

}
catch (...)
{
  // No Return
  SYD_systemError(IString("mnt_Screen in catch...some uncaught exception"));
}
```

P7002.03 CIP1                                                              PATENT

36
}

/* Function to read video memory */

5    void
     mnt_ScreenTransfer::screenCapture()
     {
       NG_TRACE_FUNC();

10         unsigned char      *p_dive = NULL;
           unsigned char      *p_current = NULL;
           unsigned int       line = 0;
           unsigned int       i = 0;
           unsigned char      mono_pixels = 0;
15

// remove the pointer from the screen.
           WinShowPointer(HWND_DESKTOP, false);

20         p_dive= (unsigned char *)v_p_diveFrameBuffer;
           p_current= v_currentScreenBuffer;

if ((v_pixelsPerByte == 8) && (v_platform ==
           syt_Programmer::c_486Color9790)) {
25
              // BW on Color 9790 Screen capture
              for(line = 0; line < v_maxScreenPixelsY; line++)
              {
                for(i = 0; i < v_maxScreenPixelsX; i++)
30              {
                    mono_pixels <<= 1;

P7002.03 CIP1                                              PATENT 37
                if (*p_dive++)
                {
                    mono_pixels |= 1;
                }
5
                if ((i % 8) == 7)
                {
                    *p_current++ = mono_pixels;
                }
10          }
            p_dive+= mnc_486CUnusedDiveSection;;
        }
    } // end on if 486C and color off else if (v_pixelsPerByte == 8) {
15
        // 386/486EL platform 9790 Screen capture
        for(line = 0; line < v_maxScreenPixelsY; line++)
        {
20          for(i = 0; i < v_bytesPerRow; i++)
            {
                *p_current++ = *p_dive++;
            }
        }
25  } //end if 386/486EL else if (v_pixelsPerByte == 1)
    {

30      // Color Screen capture
        /* Copy data from the frame buffer to the memory bitmap. */

P7002.03 CIP1                                                              PATENT

38 for(line = 0; line < v_maxScreenPixelsY; line++)
          {
            for(i = 0; i < v_maxScreenPixelsX; i++)
            {
              *p_current++ = *p_dive++;
            } // end "for" to copy x p_dive+= mnc_486CUnusedDiveSection;;
          } // end "for" to copy y } // end if 486C and color on else {
          SYD_systemError(IString("in screen compare and v_pixelsPerByte not 8 nor 1") +
               IString(v_pixelsPerByte));
        }

// display the pointer on the screen.
        WinShowPointer(HWND_DESKTOP, true);
      }

/* Function to find changed rectangles */
      void
      mnt_ScreenTransfer::screenCompare()
      {
        NG_TRACE_FUNC();

unsigned int index;

P7002.03 CIP1							PATENT

39

```
         unsigned char current;

//    printf("The screenCompare is executing.\n");

5       index = 0;
         while (index < v_screenSizeInBytes)
         {
             // compare algorithm is to compare and if different,
             // copy "current" into "previous" and set a
10           // flag in screenChangedFlagBuffer
             current = v_currentScreenBuffer[index];
             if (current != v_previousScreenBuffer[index])
             {
                 v_previousScreenBuffer[index] = current;
15               v_screenChangedFlagBuffer[index] = 0xFF;
             }
             index++;

20       } // end while index < screenSizeInBytes

//    printf("The screenCompare is exiting.\n");
         }
```

What is claimed is:

1. A communication system to transfer medical data from a patient site to a remote site, comprising:
   a hub operating as a communications platform and having a network connection to accommodate real time transfer of various types of data;
   a communications network coupled to the hub;
   a programmer for modifying an implantable medical device coupled to the hub, the programmer having a display for physiological data received from an implantable medical device and providing programmer-displayed physiological data to the hub for transfer over the communications network;
   a video device to obtain video-formatted data at the patient site, said video device being coupled to the hub and providing the video-formatted data to the hub for transfer over the communications network; and
   a receiving device at the remote site coupled to the communications network to receive the video-formatted data and the programmer-displayed physiological data from the communications network and to provide communications to the programmer from the remote site.

2. The system of claim 1, wherein the receiving device includes display means for allowing the video-formatted data to be viewed at the remote site.

3. The system of claim 2, wherein the video-formatted data includes an audio signal, and wherein the receiving device includes an audio system to allow the audio signal to be monitored at the remote site.

4. The system of claim 3, wherein the display means includes means for allowing the video-formatted data to be viewed in substantially real-time.

5. The system of claim 2, and further comprising at least one medical device to obtain medical information from a patient at the patient site, and coupled to transfer the medical information to the communications network, and wherein the receiving device is adapted to monitor the medical information.

6. The system of claim 5, wherein the display means includes means for allowing the medical information to be viewed on the display screen.

7. The system of claim 6, wherein the at least one medical device includes a fluoroscopy device.

8. The system of claim 6, wherein the at least one medical device includes a device for obtaining an electrocardiograph (ECG) signal.

9. The system of claim 1, wherein the display means includes means for displaying the display screen data.

10. The system of claim 9, wherein the display means includes means for displaying the display screen data in substantially real-time.

11. The system of claim 9, wherein the display means includes means for allowing a user to activate multiple displays simultaneously, each of the displays for displaying one or more of the screen data, the medical data, and the video-formatted data.

12. The system of claim 9, wherein the programmer includes a cursor that may be controlled at the patient site, wherein the programmer includes means for transferring first cursor information indicative of cursor control at the patient site to the communications network, and wherein the display means includes means for using the first cursor information to monitor the control of the cursor at the patient site.

13. The system of claim 12, wherein the receiving device includes mean for allowing the cursor to be controlled at the remote site, wherein the receive device includes means for transferring second cursor information indicative of cursor control at the remote site to the communications network, and wherein the programmer includes means for using the second cursor information means to monitor the control of the cursor at the remote site.

14. The system of claim 9, wherein the programmer is coupled to the at least one medical device and to the video device, and the hub is implemented on the programmer to route data between each of the video device and the at least one medical device and the communications network.

15. The system of claim 9, and further comprising a device to receive an audio signal, the device being coupled to transfer the audio signal to the communications network, and wherein the receiving device includes an audio system to allow the audio signal to be monitored at the remote site.

16. The system of claim 9, and further including at least one additional receiving device located at a second remote site coupled to receive one or more of the video-formatted data, the display screen data and the device data from the communications network, and whereby the one or more of the video-formatted data, the display screen data and the device data may be monitored at the second remote site.

17. The system of claim 1, wherein the programmer includes means for transferring to the communications network only display screen data associated with changes occurring during a predetermined time interval.

18. The system of claim 1, wherein the hub is a stand-alone data processing system.

19. The system of claim 18, wherein the hub includes communication stack means for routing the data between the communications network and each of the video device and the programmer.

20. A system to transfer medical data from a patient site to a remote site, comprising;
   a first communications network;
   a hub operating as a communications platform and having a network connection accommodating real time transfer of various types of data;
   a programmer for an implantable medical device coupled to the hub, the programmer having a display for physiological data received from an implantable medical device and providing programmer-displayed physiological data to the hub for transfer over the first communications network;
   a video device to obtain video-formatted data at the patient site, said video device being coupled to the hub and providing the video-formatted data to the hub for transfer over the first communications network;
   a first communications channel coupled to the first communications network;
   a second communications network coupled to the first communications channel;
   a second communications channel coupled to the second communications network; and
   a data processing system at the remote site coupled to the second communications channel, the remote data processing system accessing programmer-displayed physiological data and video-formatted data and transmitting modification instructions to the patient site.

21. The system of claim 20 wherein the first communications channel comprises a modem.

22. The system of claim 20 wherein the second communications network comprises an interface connection selected from a group consisting of an internet, intranet, extranet, or world-wide-web connection.

23. The system of claim 20 wherein the second communications channel comprises a phone line and a modem.

24. A system to transfer medical data from a patient site to a remote site, comprising:

a communications network;

a hub operating as a communications platform and having a network connection accommodating real time transfer of various types of data;

a programmer for an implantable medical device coupled to the hub, the programmer having a display screen with a control cursor movable on the screen, the programmer obtaining data from an implantable medical device for display on the screen and creating physiological waveform data for display on the screen, the programmer providing implantable medical device data and physiological waveform data to the hub for transfer over the communications network and providing control cursor movement data to the hub for transfer over the communications network, the implantable medical device data, physiological waveform data, and the control cursor movement data being provided in a packet description of displayed screen data;

a video device to obtain video-formatted data at the patient site, said video device being coupled to the hub and providing the video-formatted data to the hub for transfer over the communications network; and a data processing system at the remote site coupled to the communications network, the remote data processing system accepting implantable medical device data, physiological waveform data, video-formatted data, and programmer control cursor movement data, the data processing system having a display screen to reproduce implanted medical device data, physiological waveform data, video-formatted data, and programmer control cursor movements.

25. The system of claim 24 wherein the packet description of displayed screen data comprises a packet describing the physiological waveform data and a separate packet describing the location of the control cursor.

26. The system of claim 25 wherein the programmer comprises means for selectively disabling transfer of the programmer control cursor data over the communications network.

27. The system of claim 25 wherein the data processing system comprises means for selectively disabling transfer of the programmer control cursor data over the communications network.

28. The system of claim 25 wherein the data processing system comprises means for selectively viewing the video-formatted data on the display screen.

29. The system of claim 25 further comprising means for selectively viewing the video-formatted data on the display screen that include a user interface that permits a user to toggle between a video display window and a data display window on the display screen.

30. The system of claim 29 wherein the user interface permits a user to simultaneously show a video display window and a data display window on the display screen.

31. The system of claim 30 wherein the user interface includes a display screen icon utilized to select the manner in which the windows are displayed.

* * * * *